(12) United States Patent
Leeflang et al.

(10) Patent No.: US 9,937,319 B1
(45) Date of Patent: Apr. 10, 2018

(54) SLITTABLE CATHETERS AND METHODS FOR MAKING AND USING THEM

(71) Applicants: Stephen A. Leeflang, Sunnyvale, CA (US); Christian S. Eversull, Palo Alto, CA (US)

(72) Inventors: Stephen A. Leeflang, Sunnyvale, CA (US); Christian S. Eversull, Palo Alto, CA (US)

( * ) Notice: Subject to any disclaimer, the term of this patent is extended or adjusted under 35 U.S.C. 154(b) by 715 days.

(21) Appl. No.: 13/716,055

(22) Filed: Dec. 14, 2012

Related U.S. Application Data

(60) Provisional application No. 61/570,304, filed on Dec. 14, 2011.

(51) Int. Cl.
*A61M 25/00* (2006.01)

(52) U.S. Cl.
CPC ...... *A61M 25/0043* (2013.01); *A61M 25/005* (2013.01); *A61M 25/0013* (2013.01)

(58) Field of Classification Search
CPC ...... A61M 25/0668; A61M 2025/0675; A61M 2025/0034; A61M 25/0051; A61M 25/005; A61M 25/0013; A61M 25/0043
USPC .................................................. 604/164.05
See application file for complete search history.

(56) References Cited

U.S. PATENT DOCUMENTS

| | | | | |
|---|---|---|---|---|
| 2005/0182387 A1* | 8/2005 | Webler | ............. | A61M 25/0668 604/527 |
| 2007/0167930 A1* | 7/2007 | Eversull et al. | ............. | 604/524 |
| 2009/0043285 A1* | 2/2009 | Stehr | ................... | A61M 25/005 604/527 |
| 2010/0100044 A1* | 4/2010 | Ye | ..................... | A61M 25/0668 604/164.05 |
| 2010/0268196 A1* | 10/2010 | Hastings | ........... | A61M 25/0012 604/527 |

* cited by examiner

*Primary Examiner* — Matthew F DeSanto
(74) *Attorney, Agent, or Firm* — William A. English; Vista IP Law Group LLP

(57) ABSTRACT

Apparatus, systems, and methods are provided for delivering a lead or other instrument into a patient's body using a tubular device including a proximal end, a distal end sized for introduction into a body lumen, and a lumen extending therebetween, thereby defining a longitudinal axis. The tubular device includes a sidewall surrounding the lumen including a reinforcing layer embedded in one or more layers of base material, and a slittable seam in the sidewall extending from the proximal end partially towards the distal end substantially parallel to the longitudinal axis. In addition, slitter devices are for slitting, splitting, or opening the slittable seam. Methods are also provided for making catheters or other tubular devices including slittable, e.g., re-welded longitudinal seams that may be preferentially slit, split, or otherwise opened.

13 Claims, 8 Drawing Sheets

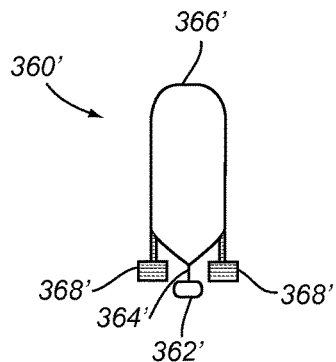
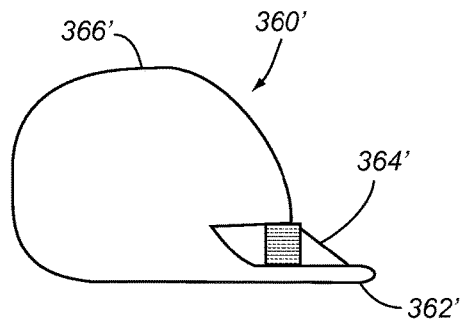
FIG. 9A     FIG. 9B
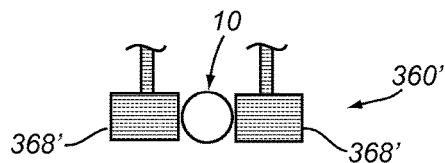
FIG. 9C
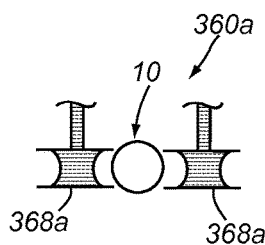 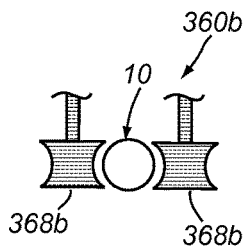 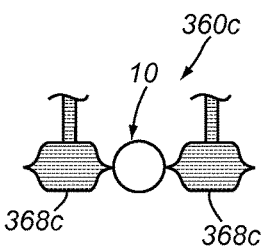 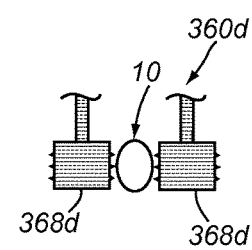
FIG. 10A     FIG. 10B     FIG. 10C     FIG. 10D
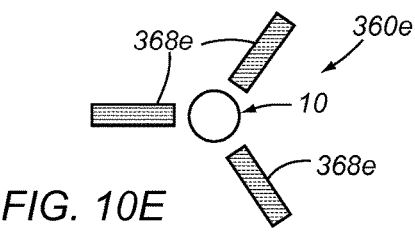
FIG. 10E

SLITTABLE CATHETERS AND METHODS FOR MAKING AND USING THEM

RELATED APPLICATION DATA

This application claims benefit of provisional application Ser. No. 61/570,304, filed Dec. 14, 2011, the entire disclosure of which is expressly incorporated by reference herein.

FIELD OF THE INVENTION

The present invention relates generally to catheters, sheaths, or other tubular devices, and, more particularly, to slittable catheters, sheaths, or other tubular devices, e.g., including slittable portions, to methods for making such tubular devices, and to systems and methods including catheters, sheaths, or other tubular devices and slitter devices.

BACKGROUND

In a variety of minimally invasive procedures, it is desirable to remove a delivery catheter, cannula, or other delivery device while leaving in place another apparatus that has been delivered through the lumen of the delivery device. For example, a pacing lead may be delivered to a chamber or vessel of the heart through a pre-shaped or steerable delivery catheter. Subsequently, the lead is left in place while the delivery catheter is removed. In the event that the proximal end of the lead is larger than its distal end, and larger than the inner diameter of the delivery catheter, the delivery catheter must be removed by splitting, cutting, slitting, or otherwise interrupting its circumference such that the lead can exit the catheter when the catheter is withdrawn from the body.

In many cases, this removal step can be difficult. In particular, if performed incorrectly by the operator, it can result in dislodgement of the implanted lead, making therapy ineffective or requiring that the procedure be repeated in order to re-implant the lead. Lead dislodgement is one of the most frustrating and clinically problematic outcomes encountered in lead delivery. When the lead is dislodged, a procedure, which may have taken hours to get to the point of slitting, must in many cases be restarted essentially from the beginning.

One such mechanism of dislodgment that commonly occurs with currently marketed slittable catheters is "spiral slitting," meaning that the slitting or cutting action cannot be sufficiently controlled by the physician to maintain a straight line of cutting (i.e., in a single line substantially parallel to the central axis of the catheter being slit). Instead, the line of slitting propagates at least partially in a non-linear (e.g., helical) path of variable direction and/or pitch.

The degree of spiral slitting may depend on a variety of factors, including how the operator holds the slitter relative to the delivery catheter. However, in the context of the procedure, its technical difficulty, and the many demands on the physician's attention, spiral slitting continues to be a widespread and contributory to the incidence of lead dislodgment.

Because the slitter is held in the physician's hand, it is substantially rotationally fixed, such that the consequence of spiral slitting is that the portion of the catheter distal to the slitter must inevitably rotates in sync with the direction, pitch, and speed of the slitting. This rotation, especially in the case of catheters with large shape set curves, can transfer excessive and/or irregular forces to the lead, increasing the likelihood of lead dislodgement. For example, as slitting proceeds in a non-linear path, it may cause the distal end of a pre-shaped or deflected catheter to rotate, which can both pull on the lead body and cause a significant change in path length from the percutaneous access site to the target delivery location of the lead tip. In particular, the path length may change significantly as the tip of a pre-shaped or deflected catheter rotates freely and unconstrained in an open chamber of the heart, commonly the right atrium, which occurs as the proximal portion of the delivery sheath is slit. As the delivery catheter is further withdrawn and its distal segment passes through generally narrowing vessels toward the access site, it becomes increasingly constrained, limiting the path length change caused by rotation. In any case, rotation of the delivery catheter may result in the lead tip moving from its target delivery location, i.e., becoming dislodged.

One common approach to the issue is using a peelable, rather than slittable, catheter. Peelable catheters include a natural parting line or weakened segment such that when pulled apart manually, the circumferential catheter body splits into two parts and allows the implanted device to exit. One problem with such catheters is that they generally lack a reinforcing structure such as a braid, coil, and the like, since such structures cannot be easily broken by hand. In contrast, slittable catheters generally include such a reinforcing structure, which can be cut with a sharp blade, scissors, or other cutting element. Unreinforced peelable catheters, however, suffer with respect to key performance elements, including kink resistance, torque, pushability, and tracking compared to reinforced catheters and so are generally disfavored. Further, materials such as PTFE are commonly used in peelable catheters since they can be scored and tend to propagate a tear line once initiated, however, materials with more favorable and mechanical characteristics, such as strength, resiliency, and variable Durometer (e.g., polyether block amide (PEBA), nylon, urethane, etc.), do not peel or tear as easily.

Therefore, catheters, sheaths, or other tubular devices that reduce the risk of spiral slitting or other problems would be useful.

SUMMARY

The present invention is directed to catheters, sheaths, or other tubular devices, e.g., including slittable portions. More particularly, the present invention is directed to slittable catheters, sheaths, or other tubular devices, e.g., including slittable portions, to methods for making such tubular devices, and to systems including catheters, sheaths, or other tubular devices and slitter devices and to methods for using such systems.

In accordance with one embodiment, a catheter, sheath, or other tubular device may be provided that includes an interrupted, i.e., not circumferentially continuous, or substantially weakened reinforcing layer, e.g., braid, to facilitate controlled slitting in a substantially straight path along at least a proximal portion of the tubular device.

In an exemplary embodiment, a reinforcing braid of a catheter may be interrupted, e.g., by pre-slitting, along a substantially linear path substantially parallel to the central longitudinal axis of the catheter and extending at least partially along the length of the catheter from the proximal end. The catheter may then be expanded, e.g., by placing the pre-slit catheter on a slightly larger mandrel, to separate longitudinal edges of the slit and form a small gap along the line of reinforcing layer interruption. The gap may then be at least partially filled with material, e.g., one or more materials that encourage susceptibility to slitting or splitting, to provide a circumferentially continuous catheter. In addition or alternatively, one or both of the longitudinal edges may be coated with desired material, e.g., to provide incomplete or partial bonding of the longitudinal edges and/or the filler material. Because the filled gap is relatively narrow compared to the circumference of the catheter, and the reinforcing braid is present around a majority of the circumference, the catheter may perform substantially like a braid reinforced catheter, e.g., with respect to torquability, kinking, and/or other performance characteristics, as discussed elsewhere herein. Moreover, if the outer layer materials of the catheter are of relatively high Durometer, e.g., nylon 12 and/or 72D PEBA, the relative contribution of the braid to the mechanical characteristics of the catheter may be generally less than the outer layer.

In one embodiment, the gap may be filled with filler material, e.g., of generally low Durometer, lower than that of the catheter shaft. For example, the proximal catheter shaft may be constructed primarily of 72D PEBA or nylon 12 and the gap may be filled with PEBA of 55D or lower Durometer filler material. The elastic mismatch between materials encourages the catheter to separate along the line of the filled gap as outward radial stress is applied to the catheter (other combinations of material may be used, e.g. relatively lower Durometer body and higher Durometer gap filler, or materials that otherwise do not adhere well to one another or tend to separate under stress).

Radial stress may be applied to the catheter by a slitting tool that includes a wedge portion. As the slitting tool is advanced through the catheter, the wedge tends to expand the filled gap, separating the edges of the cut braid. The low Durometer gap filler material may be generally weaker than the remaining circumference of the catheter shaft and tear as the wedge type slitting tool is advanced through the catheter. Alternatively, in another embodiment, the wedge may be followed by a blade. The wedge may expand the gap, separating the edges of the cut braid, and the blade may cut any gap filler material that has not been torn by radial expansion of the catheter. Additionally, it may be desirable for the braid interruption/gap to terminate within an intermediate or distal portion of the catheter (e.g., where the shaft construction changes to one including softer materials, e.g., of a Durometer similar to the gap filler material).

As discussed above, spiral slitting through the proximal portion of the catheter may be less likely to cause lead dislodgement. Thus, constructions to resist spiral slitting may not be as critical in the distal portion of the catheter. Even when there is no interruption in the braid, a slitting tool including a blade may cut through the uninterrupted catheter shaft beyond the portion including a seam, as would be the case in conventional slitting.

In accordance with an exemplary embodiment, a method is provided for making a tubular device that includes forming an elongate tubular member comprising a proximal end, a distal end, and a lumen extending therebetween, thereby defining a longitudinal axis, the tubular member comprising a side wall comprising a reinforcing layer embedded in a layer comprising base material surrounding the lumen; creating a longitudinal slit through the side wall from the proximal end at least partially towards the distal end; and filling the slit with filler material having different mechanical properties than the base material, thereby providing a slittable seam extending from the proximal end at least partially towards the distal end.

In accordance with an exemplary embodiment, a method is provided for making a tubular device that includes forming an elongate tubular member comprising a proximal end, a distal end, and a lumen extending therebetween, thereby defining a longitudinal axis, the tubular member comprising a side wall comprising a reinforcing layer embedded in a layer comprising base material surrounding the lumen; creating a longitudinal slit through the side wall from the proximal end at least partially towards the distal end; and re-welding longitudinal edges of the slit, thereby providing a slittable seam extending from the proximal end at least partially towards the distal end.

In accordance with another embodiment, a tubular device is provided that includes a proximal end, a distal end sized for introduction into a body lumen, and a lumen extending between the proximal and distal ends, thereby defining a longitudinal axis. In addition, the tubular device may include an inner liner surrounding the lumen and defining an inner surface; a reinforcing layer surrounding the inner liner, the reinforcing layer comprising a circumferentially discontinuous portion extending from the proximal end towards the distal end at a predetermined circumferential location around the circumference of the reinforcing layer; and an outer layer surrounding the reinforcing layer and comprising base material and opposing longitudinal edges extending substantially parallel to the longitudinal axis adjacent the predetermined circumferential location, the longitudinal edges re-welded together to provide a substantially continuous outer surface for the tubular device, thereby defining a longitudinal seam in the tubular device.

In accordance with still another embodiment, a tubular device is provided that includes a proximal end, a distal end sized for introduction into a body lumen, and a lumen extending between the proximal and distal ends, thereby defining a longitudinal axis. In addition, the tubular device may include a sidewall surrounding the lumen comprising a reinforcing layer embedded in one or more layers of base material; and a slittable seam in the sidewall extending from the proximal end towards the distal end substantially parallel to the longitudinal axis, the slittable seam comprising filler material that has different mechanical properties than the base material.

In accordance with yet another embodiment, a system is provided for delivering a lead or other instrument into a patient's body that includes a tubular device including a proximal end, a distal end sized for introduction into a body lumen, and a lumen extending between the proximal and distal ends, thereby defining a longitudinal axis. The tubular device may include a sidewall surrounding the lumen including a reinforcing layer embedded in one or more layers of base material, and a slittable seam in the sidewall extending from the proximal end partially towards the distal end substantially parallel to the longitudinal axis. In addition, the system includes a slitter device for slitting, splitting, or opening the slittable seam. Optionally, the system may include a pacing lead including a distal end sized for introduction into the accessory lumen.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 9A and 9B are end and perspective views, respectively, of yet another exemplary embodiment of a slitter device including stabilization rollers.

FIG. 9C is a detail of the slitter device of FIGS. 9A and 9B, showing the stabilization rollers engaging a tubular member being slit by the slitter device.

FIGS. 10A-10H are details of alternative embodiments of stabilization elements that may be provided on a slitter device, such as those shown in FIGS. 8-9C.

DETAILED DESCRIPTION OF THE EXEMPLARY EMBODIMENTS

Figure 1:
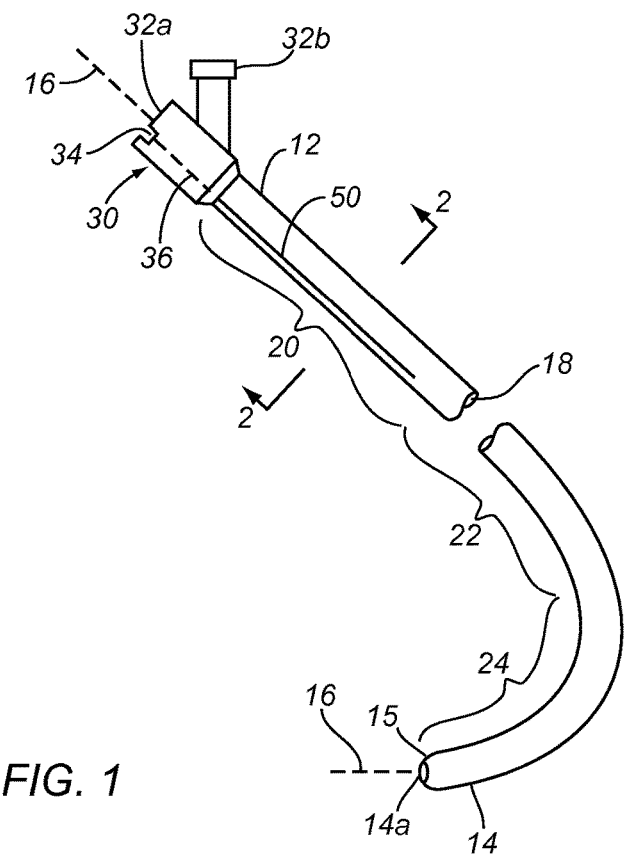
FIG. 1 is a perspective view of an exemplary embodiment of a tubular device including proximal and distal ends, and a splittable proximal portion extending partially from the proximal end towards the distal end.

Turning to the drawings, FIG. 1 shows an exemplary embodiment of an apparatus 10 for accessing a body lumen (not shown) and/or for delivering one or more fluids, agents, and/or instruments (also not shown) into a patient's body. In an exemplary embodiment, the apparatus 10 may be a sheath or catheter for delivering a cardiac and/or pacing lead (not shown), e.g., through a patient's vasculature into the patient's heart, as described further elsewhere herein.

Generally, the apparatus is an elongate tubular member or device 10 including a proximal end 12, a distal end 14 sized for insertion into a body lumen, a central longitudinal axis 16 extending between the proximal and distal ends 12, 14, one or more lumens 18 extending between the proximal and distal ends 12, 14, and a slittable seam 50 extending at least partially from the proximal end 12 towards the distal end 14. For example, the tubular member 10 may include an accessory lumen 18 sized for receiving or carrying one or more instruments or other elements (not shown) therethrough. As shown in FIG. 1, the seam 50 may extend only partially from the proximal end 12 towards the distal end 14. Further, relative to the sidewall or cross-section of the tubular member 10, the seam 50 may extend from an outer surface 11 of the tubular member 10 to the inner surface 19 of the accessory lumen 18, e.g., as shown in FIG. 2C and as described further elsewhere herein.

The tubular member 10 may have a length sufficient to access a desired location within a patient's body. For example, the length may be sufficient to extend from a percutaneous access site, such as a femoral artery, carotid artery, and the like, through the patient's vasculature to a target location, e.g., a vessel within the patient's heart, such as a coronary vein accessed through the right atrium and coronary sinus. In exemplary embodiments, the length of the tubular member 10 may be between about five and one hundred twenty centimeters (5-120 cm) or between about thirty and sixty five centimeters (30-65 cm). In addition, the tubular member 10 may have an outer diameter that allows access to a target location, e.g., between about four and twenty five French (1.3-8.3 mm), or between about four and fifteen French (1.3-5.0 mm).

In exemplary embodiments, the accessory lumen 18 may be sized for receiving or carrying a cardiac or pacing lead, guide wire, procedure catheter, or other instrument (not shown) therethrough, e.g., having a diameter between about one and five millimeters (1-5 mm). The accessory lumen 18 generally extends from the proximal end 12 along the length of the tubular member 10 to an outlet 14a in the distal end 14. Optionally, the tubular member 10 may include one or more additional lumens (not shown), e.g., a guidewire lumen, infusion lumen, steering element lumen, and the like (not shown), adjacent the accessory lumen 18.

The distal end 14 may include a tapered, rounded, or otherwise shaped distal tip 15, e.g., to provide a substantially atraumatic tip and/or to facilitate advancement or navigation through various anatomy.

Optionally, as shown in FIG. 1, the proximal end 12 may include a handle or hub 30 including one or more ports, e.g., an axial port 32a communicating with the accessory lumen 18 and a side port 32b for infusing fluids into the accessory lumen 18, e.g., around an instrument (not shown) inserted through the axial port 32a into the accessory lumen 18. The port(s) 32 may include one or more valves, e.g., a hemostatic valve (also not shown), which may provide a substantially fluid-tight seal, while accommodating insertion of one or more instruments or fluids into the accessory lumen 18. In addition or alternatively, the port(s) 32 may include one or more connectors, such as a Luer lock connector, for connecting other devices (not shown) to the hub 30, e.g., for connecting a syringe or other source of fluid (not shown) to the side port 32b communicating with the accessory lumen 18.

Optionally, the hub 30 may also include one or more actuators, such as sliders, buttons, switches, and the like, e.g., for activating and/or manipulating any components (also not shown) on the distal end 14 or otherwise operating the apparatus 10, e.g., for steering the distal end 14, as described elsewhere herein. In addition or alternatively, the hub 30 may include one or more features, e.g., a notch 34 and/or a weakened region 36 aligned with the seam 50, for facilitating slitting the apparatus 10 during use, as described elsewhere herein.

Generally, with particular reference to FIG. 2C, the tubular member 10 may include an inner liner 40, e.g., at least partially surrounding or otherwise defining the accessory lumen(s) 18, a reinforcement layer 42 surrounding the liner 40, and an outer jacket or layer 44 surrounding and/or incorporating the reinforcement layer 42. All or some of the layers may extend at least partially between the proximal and distal ends 12, 14, e.g., entirely between the proximal and distal ends 12, 14, as described elsewhere herein. The reinforcement layer 42 and/or outer layer 44 may be attached to the liner 40, e.g., by laminating, adhering, adhesive bonding, ultrasonic welding, reflowing or other heating, and the like, e.g., as disclosed in U.S. Pat. Nos. 7,550,053, 7,553,387, and 8,070,898, and in U.S. Publication Nos. 2009/0126862, and 2010/0211025, the entire disclosures of which are expressly incorporated by reference herein. Optionally, the tubular member 10 may include one or more additional layers (not shown), if desired, e.g., between the liner 40 and the reinforcing layer 42.

The liner 40 may at least partially surround the accessory lumen 18, e.g., other than at the seam 50, and/or may extend substantially entirely along the length of the tubular member 10. The liner 40 may be formed from material having desired properties and/or including an inner surface 19 having one or more coatings thereon. For example, the liner 40 may be formed from thermoplastic or other polymeric materials, e.g., polyolefin, PEBAX, nylon, silicone, polypropylene, polyethylene, and the like, including one or more coatings on the inner surface 19, e.g., a hydrophilic and/or lubricious coating, as disclosed in the references incorporated by reference elsewhere herein. Alternatively, the liner 40 may be formed from lubricious material, such as PTFE or FEP, although thermoplastic materials, such as PEBAX, have the advantage of being able to reflow back together easily during processing.

The reinforcement layer 42 may include one or more reinforcing elements wound, for example, in a braided or helical configuration around the liner 40, e.g., in a substantially continuous manner other than at the seam 50, as described further elsewhere herein. For example, the reinforcement layer 42 may include one or more, e.g., a plurality of, round or flat wires, filaments, strands, and the like, initially wound entirely around the circumference of the liner 40 and/or at least partially along the length of the tubular member 10, e.g., to provide a braid of overlapping elements. During the process in which the seam 50 is created, the reinforcing elements may be cut or otherwise separated along the length of the seam 50, e.g., to provide a circumferential discontinuity in the reinforcing layer 22 that extends substantially parallel to the longitudinal axis 16.

In an alternative embodiment, one or more features may be incorporated into the braid or other arrangement of reinforcing elements along the seam 50, e.g., to facilitate cutting or otherwise severing reinforcing elements that cross the location of the seam 50. For example, when the reinforcing elements are braided around the liner 40, one or more tri-axial elements (not shown) may be incorporated into the braid along the location for the seam 50, e.g., such that reinforcing elements pass over and/or under the tri-axial elements. Once the braid is complete and/or an outer layer is applied around the braid, the tri-axial elements may be removed, e.g., pulled so as to shear at least one layer of wires in the braid, thereby at least partially severing reinforcing elements along the location of the seam 50. In an exemplary embodiment, the tri-axial elements are elongate triangular cross-sectional rods or tubes that include sharpened apices such that the apices cut or otherwise sever contacted reinforcing elements along the location of the seam 50.

The reinforcing elements may be formed from metal, such as stainless steel, Nitinol, and the like; polymers, such as PEEK, HDPE, UHMWPE, and the like; other fibers, such as glass, Kevlar, and the like; or composite materials. The reinforcement layer 42 may be configured to substantially transfer torsional forces between the proximal and distal ends 12, 14, e.g., to allow the tubular member 10 to be twisted from the proximal end 12 to rotate the distal end 14 about the longitudinal axis 16 within a patient's body. In addition, the reinforcement layer 42 may substantially transfer axial forces, e.g., to allow the distal end 14 of the tubular member 10 to be advanced or otherwise manipulated within a patient's body from the proximal end 12 without substantial risk of buckling and/or kinking, and/or may provide hoop strength, e.g. to resist crushing.

The outer layer 44 may include one or more layers wrapped around, placed over, or otherwise disposed and attached around the reinforcing layer 42, e.g., to at least partially embed the reinforcing layer 42 within the outer layer 44. For example, the outer layer 44 may include one or more tubular layers (not shown) placed over the reinforcement layer 42 and/or one or more sheets wrapped around the reinforcement layer 42, e.g., as disclosed in the references incorporated by reference elsewhere herein. Exemplary base materials that may be used in the outer layer 44 include thermoplastics, such as doped or undoped PEBA, urethane, and nylon (including nylon 6/6, nylon 11, nylon 12), and/or engineered resins (including Zytel, Rilsan, Grilamid, Vestamid), polyethylene, polyvinylchloride, fluoropolymers (including PTFE, FEP, PFA, PVDF, THV, ETFE, ECFE), polyethylene terepthalate polyester, polyetheretherketone, polypropylene, silicone, natural and synthetic rubbers, polystyrene, polycarbonate, polymethylmethacrylate, and the like.

With continued reference to FIG. 1, one or more of the layers of the tubular member 10 may have a substantially homogenous construction between the proximal and distal ends 12, 14. Alternatively, the construction may vary along the length of the tubular member 10 to provide desired properties, e.g., between proximal, intermediate, and/or distal portions 20, 22, 24 of the tubular member 10. For example, the proximal portion 20 of the tubular member 10 adjacent the proximal end 12 may be substantially rigid or semi-rigid, e.g., including relatively high Durometer and/or stiffness materials that provide sufficient column strength to allow the distal end 14 of the tubular member 10 to be pushed and/or otherwise manipulated from the proximal end 12. In contrast, the distal portion 24 may be substantially flexible, e.g., including relatively low Durometer and/or flexible materials that facilitate advancement through tortuous anatomy. Such variations may be achieved by changing materials of the liner 40, the outer layer 44, and/or by changing the configuration and/or presence of the reinforcing layer 42 along the length of the tubular member 10, e.g., similar to embodiments disclosed in the references incorporated by reference elsewhere herein.

In an exemplary embodiment, the distal portion 24 of the tubular member 10 may be biased to a predetermined shape, e.g., a substantially constant radius arc, or a more complicated curved or curvilinear shape. Thus, the distal portion 24 may be biased to a predetermined shape but may be sufficiently flexible to allow advancement and/or manipulation within the patient's vasculature or other body lumens. Optionally, the distal portion 24 may be steerable if desired, i.e., may be curved or otherwise deflected substantially within one or more steering planes. In this alternative, one or more pull wires, cables, fibers, threads, filaments, or other steering elements (not shown) may be slidably received within respective lumen(s) of the tubular member 10, e.g., including a proximal end coupled to an actuator (not shown) on the hub 30 and extending through the intermediate portion 22, into the distal portion 24.

In addition, the tubular member 10 includes a slittable, splittable, or otherwise openable seam 50 extending along the proximal portion 22, e.g., from the proximal end 12 at least partially towards the intermediate portion 22 and/or distal portion 24. For example, the seam 50 may extend from the proximal end 12 and/or hub 30 along the proximal portion 20 a predetermined distance. In exemplary embodiments, the seam 50 may have a length between about twenty five and fifty five centimeters (25-55 cm).

Optionally, the tubular member 10 may include one or more features to facilitate identifying the seam 50 and/or confirming that a substantially axial slit is being formed in the tubular member 10. For example, one or more lines or other visual markers, e.g., a continuous or discontinuous line (not shown), may be printed or otherwise provided on the outer surface of the tubular member 10 over or otherwise adjacent the seam 50 to allow a user to identify the seam 50 and/or ensure that a longitudinal slit created when the tubular member 10 is slit during a procedure occurs substantially along the seam 50, as described further below.

Figure 2A:
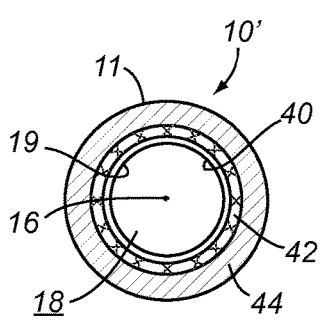
FIGS. 2A-2C are cross-sectional views of a tubular member showing a method for making the tubular device of FIG. 1, taken along line 2-2.
Figure 2B:
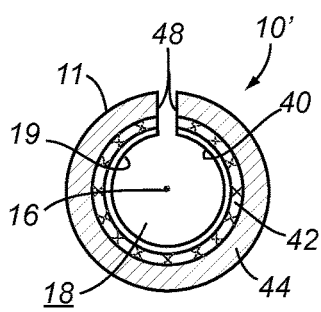
Figure 2C:
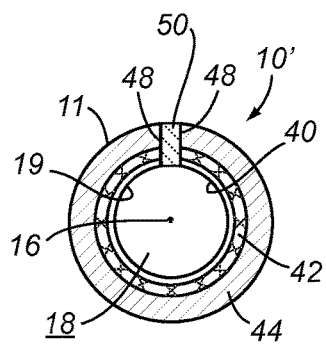

As shown in FIGS. 2A-2C and as described further below, the proximal portion 20 of the tubular member 10 may be "pre-slit" to create separated longitudinal edges 48 that are attached back together to define the seam 50 such that the tubular member 10 has an integral, non-delaminating (under normal use conditions) side wall. In one embodiment, a gap between the longitudinal edges 48 may be filled with filler material having one or more properties different than the adjacent base material, such as one or more softer (lower Durometer) materials, harder (higher Durometer) materials, more elastic materials, less elastic materials, less adherent, differing in melt temperature, melt flow index or thermoplastic properties, and the like. Exemplary materials for the filler material include nylons, urethanes, PEBAs, doped resins (e.g., doped with clay, glass, barium, tungsten, bismuth, PTFE, and the like) including PEBA, nylon, urethane, and the like where the doping creates an elasticity mismatch, decreases bond strength, or otherwise facilitates separation of the tubular member 10 along the seam 50. In other embodiments, the filler material may include high crystallinity materials, fluoropolymers (e.g., PTFE, FEP, and the like), which may be etched or otherwise surface treated; other melt-flowable materials having similar melt temperature, but reduced adhesion to the base materials of the tubular member 10, including polyethylene, HDPE, and the like; relatively elastic material compared to the base materials including low Durometer PEBA, urethane, silicone, relatively inelastic material compared to the base materials, and the like.

In an exemplary embodiment, the base material of the proximal portion 20 may have a relatively high Durometer, e.g., 72 Durometer PEBAX liner 40 and/or Vestamid/nylon outer layer 44, and the filler material may have a relatively low Durometer, e.g., 35 Durometer PEBAX. For example, the different materials may result in the filler material and/or seam 50 stretching under stress, e.g., when a slitter (not shown) is inserted into the proximal end 12, which may facilitate cutting, separating, and/or fracturing along the seam 50 to cause substantially straight slitting during use, as described further elsewhere herein.

Turning to FIGS. 2A-2C, an exemplary method is shown for making a catheter or other tubular device 10 including a slittable, splittable, or otherwise openable seam 50 that extends along the proximal portion 20. First, an initial catheter or other tubular device 10' may be formed, e.g., having a cross-section such as that shown in FIG. 2A. Exemplary constructions and methods for making such tubular devices are disclosed in the references incorporated by reference elsewhere herein. For example, the initial tubular device 10' may include an inner liner 20, a circumferentially substantially continuous reinforcing layer 22 around the liner 20, and a substantially continuous outer layer 24 surrounded the reinforcing layer 22.

As shown in FIG. 2B (and with additional reference to FIG. 1), the initial tubular device 10' is then slit, i.e., has the side wall cut entirely from the outer surface 11 to the inner surface 19 of the lumen 18, e.g., from the proximal end 12 towards the distal end substantially parallel to the longitudinal axis 16, thereby creating separated longitudinal edges 48. More particularly, the length of the slit may extend only along the proximal portion 20, e.g., having a length corresponding to the desired length of the seam 50, although alternatively, the slit may extend to the intermediate portion 22, to the distal portion 24, or entirely to the distal tip 15, if a longer seam is desired.

In the embodiment resulting in the tubular member 10 shown in FIG. 1, the intermediate and/or distal portions 22, 24 of the original tubular device 10' may remain substantially intact when the slit is created. Alternatively, as described elsewhere herein, if desired, the entire length of the tubular device 10' may be slit to create a seam that extends the entire length of the resulting tubular device (not shown). It will be appreciated that, as the tubular device 10' is slit, the reinforcing elements of the reinforcing layer 22 may be severed or otherwise separated, thereby creating a circumferential discontinuity in the reinforcing layer 22. Alternatively, if tri-axial elements and the like are provided within the reinforcing layer 42, the tri-axial elements may be removed before cutting the slit, e.g., to sever some or all of the reinforcing elements, which may facilitate creating the slit since the cutting device may not need to cut through all of the reinforcing elements along the desired seam 50.

The longitudinal edges 48 of the slit are then attached back together to close the sidewall of the tubular device 10. For example, as shown in FIGS. 2B and 2C, the longitudinal edges 48 may be spaced apart slightly to create a gap, and filler material may be attached to the longitudinal edges 48 within the gap. Once the filler material is introduced and/or attached to the longitudinal edges 48, the resulting tubular device 10 may have a substantially uniform and/or continuous outer surface 11 and/or inner surface 19, as shown in FIG. 2C. Alternatively, if desired, the final thickness of the filler material may be less or more than the thickness of the original side wall.

In an exemplary embodiment, to create the seam 50, the slit portion of the initial tubular device 10' may be placed on a mandrel (not shown) having an outer diameter that is slightly larger than the original inner diameter of the initial tubular device 10,' thereby separating the longitudinal edges 48, as shown in FIG. 2B. The filler material may then be applied into the resulting gap and attached to the longitudinal edges 48 until a substantially uniform outer surface 11 is provided along the seam 50. Once the filler material is melted, bonded, cured, or otherwise attached to the adjacent material, the mandrel may be removed. Thus, in this embodiment, the final outer diameter of the tubular member 19 may be slightly larger than the initial tubular member 10.'

The filler material may be different than the base material of the tubular device 10 to create a mismatch between the materials, which may bias or otherwise facilitate subsequent splitting, slitting, or otherwise separating the tubular member 10 along the seam 50. For example, the filler material may be 35 Durometer PEBAX or other thermoplastic material, and/or other materials described elsewhere herein, e.g., that are different than the base material(s). Such thermoplastic material may be reflowed and/or otherwise heated to bond or attach to the adjacent materials of the original layers of the initial tubular device 10.' For example, thermoplastic liner materials and/or outer layer materials may be reflowed, bonded, and/or otherwise easily attached to the filler material along the longitudinal edges 48 (referred to generally herein as "re-welded").

Alternatively, the longitudinal edges 48 may be placed against one another and attached together, e.g., without introducing any filler material between the longitudinal edges 48. In this alternative, the longitudinal edges 48 may be attached directly together, e.g., by one or more of bonding with adhesive, sonic welding, fusing, and the like. For example, sufficient heat may be applied to reflow, melt, or otherwise attached thermoplastic or other materials of the liner 20 and/or outer layer 24 together along the longitudinal edges 48. Thus, in this embodiment, the final outer diameter of the tubular member 10 may be substantially the same as the initial tubular member 10.' In this alternative, the resulting bond or seam 50 may be somewhat weaker than the original base materials defining the remainder of the circumference of the tubular member 10, e.g., such that the tubular member 10 may preferentially tear, cut, or otherwise separate along the seam 50, as described elsewhere herein. Further alternatively, the longitudinal edges 48 may be coated prior to being attached together, in order to modify their properties of adhesion.

Figure 3:
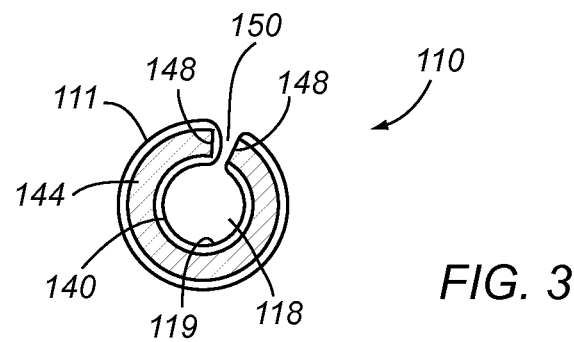
FIG. 3 is a cross-sectional view of another embodiment of a tubular device including a weakened longitudinal seam that extends along a portion of the tubular device.

Turning to FIG. 3, another exemplary embodiment of a tubular member 110 is shown that includes a longitudinal seam 150 formed in the sidewall thereof and extending at least partially between proximal and distal ends of the tubular member 110, e.g., a predetermined distance from the proximal end (not shown), similar to other embodiments herein. Unlike other embodiments, a relatively thin and/or flexible sheet, e.g., a sheet of thermoplastic and the like, including a coated outer surface, such as a hydrophilic and/or lubricious coating, may be provided that may be included in both the outer surface 111 and the inner surface 119 of the tubular member 110. For example, a single sheet may be provided that has sufficient width to cover the outer and inner surfaces 111, 119, e.g., when wrapped or otherwise applied around the surfaces.

For example, during fabrication of the tubular member 110, the coated sheet may be wrapped around a mandrel (not shown) with its coated surface oriented inwardly. The mandrel may have a diameter or other cross-section similar to the intended accessory lumen 118 of the tubular member 110. The coated sheet may be wrapped around the mandrel about its width with the excess width being held away or otherwise free from the mandrel surface. One or more reinforcing and/or outer layers or jackets may be applied around the coated sheet and mandrel, e.g., in a "C" or other configuration that extends partially or entirely around the coated sheet and mandrel but still defines spaced apart longitudinal edges 148.

During this application, the excess width of the coated sheet may between the longitudinal edges 148 and then be wrapped at least partially around the outer surface of the outer layer 144 (which may include a reinforcing layer, not shown for simplicity), e.g., with the coated surface oriented outwardly to provide an outer surface 111 including a desired lubricity and/or or other property. The sheet may be attached to the outer layer 144, e.g., by bonding, heating, fusing, sonic welding, and the like, similar to other embodiments herein. The longitudinal edges 148 may be attached together and/or filler material (not shown) may be provided between the longitudinal edges 148, e.g., similar to other embodiments herein. Any excess sheet material after wrapping the coated sheet around the entire outer circumference may be cut off or otherwise removed to provide a continuous side wall tubular member 110. Alternatively, the coated sheet may be cut off or otherwise removed immediately adjacent the seam 150, e.g., if a coated outer surface is not desired. The resulting seam 150 may include a portion of the coated sheet passing therethrough between the inner and outer surfaces 111, 119, thereby providing a weakened and/or otherwise modified seam 150 that extends substantially parallel to a longitudinal axis of the tubular member 110.

Figure 4A:
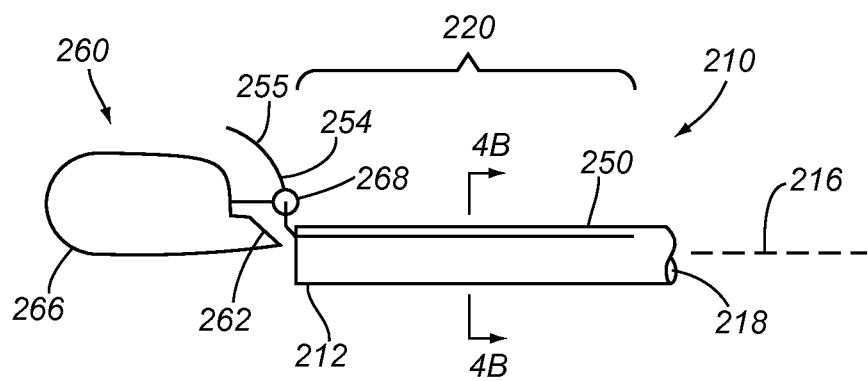
FIG. 4A is a side view of yet another embodiment of a tubular device including a longitudinal seam having a rip cord embedded therein and showing a slitter device for slitting the tubular member along the seam.
Figure 4B:
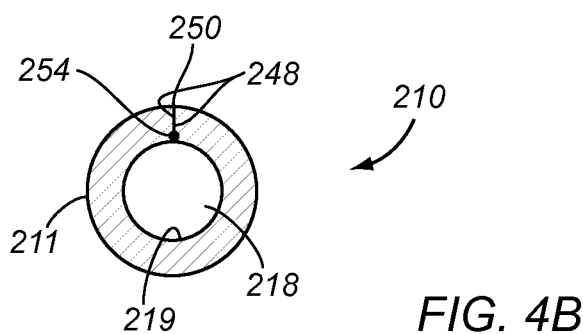
FIG. 4B is a cross-sectional view of the tubular device of FIG. 4A taken along line 4B-4B.

Turning to FIGS. 4A and 4B, yet another embodiment of a tubular device 210 is shown that includes a longitudinal seam 250 extending substantially parallel to the longitudinal axis along a slittable, e.g., proximal, portion. The tubular device 210 may be provided from an initial tubular member including a longitudinal slit cut into and through the sidewall, similar to other embodiments herein.

Unlike previous embodiments, one or more rip cords 254 may be provided in the seam 250, e.g., embedded in between longitudinal edges 248 of the tubular member 210. For example, a longitudinal slit may be formed along the desired portion, e.g., a proximal portion 220 of the tubular member 210. A rip cord 254 may be positioned between the longitudinal edges 248, e.g., such that the rip cord 254 is bonded with adhesive, fused, or otherwise secured within the resulting seam 250. Alternatively, two lengths of rip cord (not shown) may be bonded within the seam 250, e.g., adjacent the outer and inner surfaces 211, 219, for example, by providing two lengths or rip cord placed along the length of the slit and folded back along the slit again. In exemplary embodiments, the rip cord(s) 254 may be formed from elastic material and/or may be bunched, coiled, folded, and the like, e.g., to minimize impact on desired flexibility and/or torque imparted by the rip cord 254 on the flexibility or deflection of the tubular member 210.

Subsequently, if desired to open the seam 250, e.g., after using the tubular member 210 to deliver a cardiac lead or other instrument (not shown), the rip cord 254 may be pulled, thereby tearing or separating the longitudinal edges 248 to accommodate removing the tubular member 210 from around a pacing lead or other instrument (not shown). Alternatively, the rip cord 254 may only weaken or partially separate the longitudinal edges 248 of the seam 250, and then a slitter or splitting device may be used to complete separation of the seam 250.

In an exemplary embodiment shown in FIG. 4A, a slitter 260 may be provided that includes a blade 262 coupled to a handle 266. Alternatively, the slitter 260 may include a wedge or other feature (not shown) instead of or in addition to the blade 262, e.g., if the slitter is intended to cause splitting along a weakened seam 250, e.g., before or instead of cutting with the blade 262. In addition, the slitter 260 includes a guide 268, e.g., disposed above or otherwise adjacent the blade 262. The rip cord 254 may be coupled with the guide 268, e.g., slidably received through a hole or opening therein, to improve the shearing angle when the rip cord 254 is pulled (optimally substantially perpendicular to the longitudinal axis 216 of the tubular member 210). Optionally, the rip cord 2254 may include a free end 255 coupled to the proximal or distal end of the seam 250, e.g., such that the rip cord 254 may be pulled from either end to shear and/or otherwise propagate the slit distally to proximally or vice versa.

Figure 5:
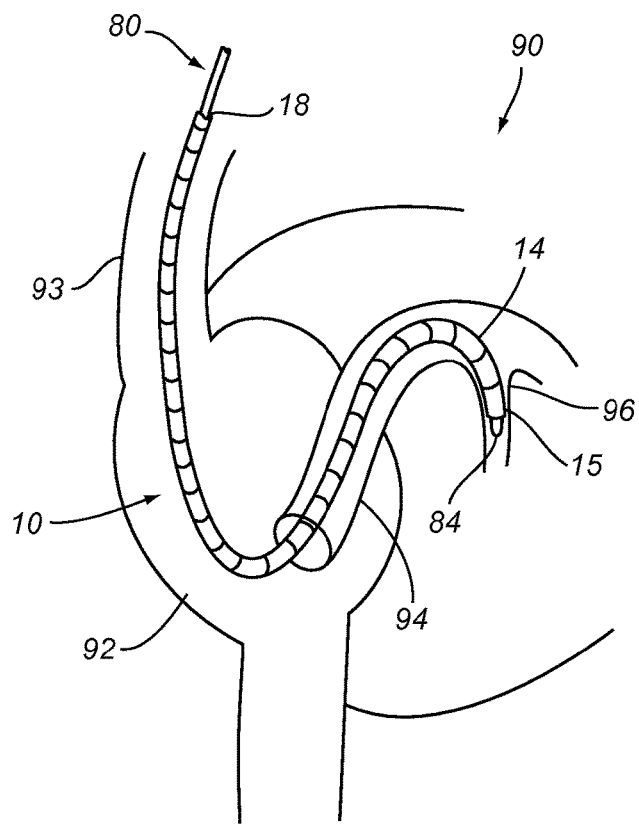
FIG. 5 is a cross-sectional view of a patient's body showing a method for delivering a pacing lead into a patient's heart using a delivery catheter, such as the tubular device shown in FIG. 1.

Turning to FIG. 5, an exemplary method is shown for using a catheter or other tubular device, such as the tubular member 10 shown in FIG. 1 (or any other embodiment herein), to deliver a pacing lead 80 into a patient's heart 90. The distal end 14 of the tubular member 10 may be introduced into the patient's body and advanced to a target location, e.g., through the right atrium 92 of the heart 90 into the coronary sinus 94 until the distal end 14 is positioned within a target coronary vessel 96 in which the lead 80 is to be delivered. If the distal portion 24 of the tubular member 10 has a pre-set shape, the tubular member 10 may rotated and/or otherwise manipulated during introduction to facilitate accessing the desired vessels between the access site and the target location, e.g., to access the coronary sinus 94 from within the right atrium 92.

Once the distal end 14 is positioned within the target vessel 96, a distal end 84 of the lead 80 may be introduced into the accessory lumen 18, e.g., through the port 32a shown in FIG. 1, and advanced until the lead distal end 84 is positioned within the distal end 14 or is deployed from the outlet 14a within the target vessel 96. For example, the accessory lumen 18 of the tubular member 10 may provide a continuous lubricious path for passing the lead 80 through intervening anatomy until the lead distal end 84 is positioned within the target vessel 96.

Once the lead distal end 84 is positioned as desired within the target vessel 96, the tubular member 10 may be withdrawn from the heart 90 and the patient's body to leave the lead 80 in position. Generally, this involves slitting the proximal end 12 of the tubular member 10 to remove the tubular member 10 over features on the proximal end of the lead 80, e.g., a hub, connectors, and the like (not shown), while withdrawing the distal end 14 from around the lead distal end 84.

In particular, with additional reference to FIG. 1, a slitting device, such as any of the slitter devices described elsewhere herein (not shown), may be aligned with the seam 50 and used to cut through the sidewall of the tubular member 10 from the proximal end 12 towards the distal end 14. If the tubular member 10 includes a hub 30, the hub 30 may include one or more features aligned with the seam 50 to facilitate the user slitting along the seam 50 rather at another location around the circumference of the tubular member 10. For example, as shown in FIG. 1, the hub 30 may include a notch 34 or other feature that may identify the circumferential location of the seam 50 where the slitting device is to be advanced. In addition or alternatively, the hub 30 may include a thin walled or otherwise weakened region 36 aligned with the seam 50 and/or notch 34 such that, when the slitting device is used to cut through the hub 30, the weakened region 36 may guide the slitting device through the hub 30 towards the seam 50.

As the slitting device encounters the seam 50, the material and/or construction of the seam 50 may cause the slitting device to be directed substantially parallel to the longitudinal axis 16 of the tubular member 10 for the length of the seam 50. Because of the substantially axial slitting of the tubular member 10 along the proximal portion 20, spiral or other rotational forces are not translated from the proximal end 12 to the distal end 14 of the tubular member 10 since the proximal end 12 may remain substantially rotationally stationary. This may minimize the risk of applying rotational or other undesired forces on the lead distal end 84 delivered within the target vessel 96 while the distal end 14 of the tubular member 10 is being at least partially withdrawn.

This may be particularly useful when the distal end 14 of the tubular member 10 remains within the "danger zone" during delivery of a pacing lead into a coronary vessel 96 within a patient's heart 90. The danger zone is generally considered the region within the patient's anatomy where the distal end 14 is unsupported within a larger vessel or an open chamber, e.g., the right atrium 92, of the heart 90, and/or where rotation can displace the distal end 84 of the lead 80. Within the danger zone, rapid and/or unpredictable movement of the distal end 14, e.g., due to spiral slitting, may cause the distal end 14 to rotate, e.g., within the coronary sinus, 94, the right atrium 92, or even within a few centimeters of the superior or inferior vena cava, which may pull or otherwise dislodge the lead distal end 84 from the target vessel 96. This may be particularly important when the distal end 14 is pre-shaped to a curvilinear shape since unexpected rotation may cause the distal end 14 to twist and then rapidly rotate once within the right atrium 92 or other location (to release the rotational stresses caused by the spiral slitting), which may pull or otherwise dislodge the lead 80.

The length of the seam 50 may be sufficient to allow the distal end 14 of the tubular member 10 to be withdrawn from the target vessel 96 into the right atrium 92 and/or into the vena cava without substantial rotational forces. Once beyond the seam 50, the slitter device may continue to slit the tubular member 10, e.g., through the intermediate portion 22 to the distal portion 24, and ultimately to the distal tip 15, thereby allowing the tubular member 10 to be removed from around the proximal end of the lead 80. If the slitter device does not continue to slit the tubular member 10 substantially axially beyond the seam 50, i.e., begins to cause spiral slitting, any rotational forces applied to the distal end 14 may not create substantial risk of dislodging the lead 80, since the distal end 14 will be located within supported locations, e.g., within the superior vena cava 93 or other location between the right atrium 92 and the access site. Thus, the tubular member 10 may be removed with minimal risk of dislodging the distal end 84 of the lead 80 within the target vessel 96.

Figure 6A:
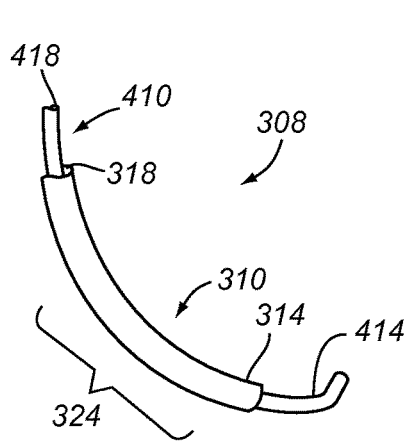
FIGS. 6A and 6B are side views of still another embodiment of a tubular device including telescoping tubular members.
Figure 6B:
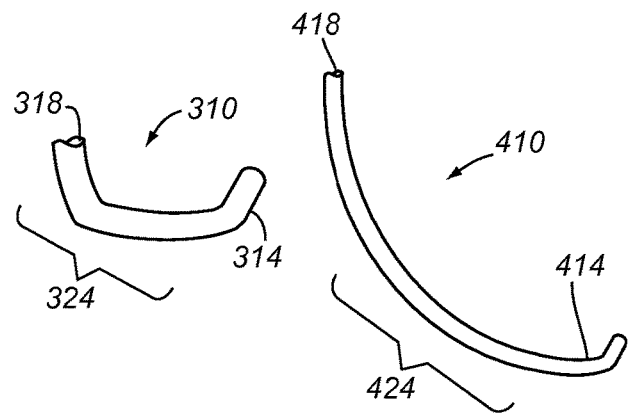

Turning to FIGS. 6A and 6B, another embodiment of an apparatus 308 is shown for accessing a body lumen and/or for delivering one or more fluids, agents, and/or instruments into a patient's body (not shown). Generally, the apparatus 308 includes a pair of telescoping catheters, e.g., an outer shape-set catheter 310 and an inner catheter 410 that is generally straight over the majority of its length. Each catheter 310, 410 generally includes a proximal end (not shown), a distal end 314, 414, and one or more lumens 318, 418 extending therebetween, similar to other embodiments herein.

Unlike other embodiments herein, the catheters 310, 410 may not include a longitudinal seam but may have a circumferentially uniform construction, although alternatively, slittable, splittable, or otherwise openable seams (not shown) may be provided in one or both catheters 310, 410. The outer catheter 310 includes a lumen 318 for slidably receiving at least a distal portion 424 of the inner catheter 410 therein, e.g., as shown in FIG. 6A. The inner catheter 410 includes an accessory lumen 418 for receiving a pacing lead or other instrument (not shown), similar to other embodiments herein.

As shown in FIG. 6B, the outer catheter 310 may include a pre-shaped distal portion 324, similar to other embodiments, e.g., biased to a predetermined curvilinear shape to facilitate accessing the coronary sinus from within the right atrium, yet sufficiently flexible to allow advancement through the patient's vasculature. The distal portion 424 of the inner catheter 410 has a substantially straight shape, yet is also sufficiently flexible to allow advancement through the patient's vasculature. The stiffness of the distal portion 424 of the inner catheter 410 may be such that it overcomes the pre-set shape of the distal portion 324 of the outer catheter 310.

For example, as shown in FIG. 6A, when the distal portion 424 of the inner catheter 410 is inserted into and/or beyond the distal portion 324 of the outer catheter 310, the assembled catheter 310, 410 may be biased to a substantially straight shape. In contrast, when the inner catheter 410 is withdrawn or the outer catheter 310 is advanced beyond the distal portion 424 of the outer catheter 410, the distal portion 324 of the outer catheter 310 may again be biased to its pre-set shape, as shown in FIG. 6B.

During use, the distal portion 324 of the outer catheter 310 may be introduced into a patient's body, e.g., from a percutaneous entry site into the right atrium (not shown). The pre-set shape of the distal portion 324 may facilitate accessing the coronary sinus and/or coronary veins (not shown), similar to other embodiments herein. Once within a target location, e.g., a coronary vein intended to receive a pacing lead, the inner catheter 410 may be introduced into the lumen 318 of the outer catheter 310 and advanced until the distal A pacing lead or other instrument (not shown) may be introduced into the accessory lumen 418 and advanced until the lead distal end is positioned within the target vessel similar to other embodiments herein. Once properly positioned, the proximal end of the outer catheter 310 may be slit first such that during retraction, the distal portion 324 substantially rides along the path defined by the distal portion 424 of the inner catheter 410. Thus, any rotation of the outer catheter 310, e.g., caused by spiral slitting, may not lead to significant change in path length, nor transfer forces to the lead since it is disposed within the inner catheter. 410. Once the outer catheter 310 is entirely slit or slit sufficiently that the distal portion 324 is beyond the danger zone, the inner catheter 410 may be slit. Because of the relaxed, substantially straight shape of the distal portion 424 of the inner catheter 410, rotational and/or other forces that may change the path length or otherwise disturb the lead may be minimized.

Alternatively, one or more stiffening elements (not shown) may be introduced into the system, e.g., a stylet, or an annular or "C" shaped member. For example, a stiffening element may be introduced over the outer catheter 310, between the lead and the inner catheter 410, and/or between the outer and inner catheters 310, 410 to support the lead and prevent unpredictable forces from the outer catheter 310 acting on the lead.

In another alternative, the primary pre-set curvilinear shape for accessing the coronary sinus (or other body lumens) may be included in the distal portion 424 of the inner catheter 410 with the distal portion 324 of the outer catheter 310 being relatively straight. Thus, in this alternative, the coronary sinus may be accessed using the inner catheter 410, and then the outer catheter 310 may be advanced forward over the inner catheter 410 for support once the coronary sinus is cannulated. The lead may then be introduced through the inner catheter 410 into the target vessel. In this alternative, the inner catheter 410 may be slit before the outer catheter 310. During slitting, the shape of the inner catheter 410 may be attenuated and/or constrained by the outer catheter 310, thereby decreasing the path length change created by any rotational slitting.

In another alternative, any catheter shape set in the distal portion may be reversible, e.g., induced by a pull wire or other steering element (not shown), and the catheter may be returned to a generally straight configuration before slitting. In still another alternative, a catheter may be provided that is partially peelable, e.g., including a proximal portion that is not braid reinforced or has a circumferentially interrupted braid (not shown). In this alternative, the user may peel the proximal portion to withdraw catheter distal portion from the "danger zone" before slitting is initiated on the unpeelable portions, e.g., distal braid reinforced sections of the intermediate and/or distal portions (also not shown).

Figure 7A:
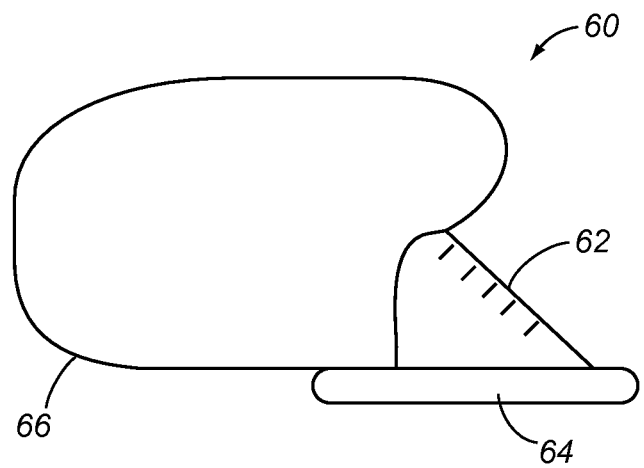
FIGS. 7A and 7B are side and end views of an exemplary embodiment of a slitter device being used to slit a longitudinal seam in a tubular member.
Figure 7B:
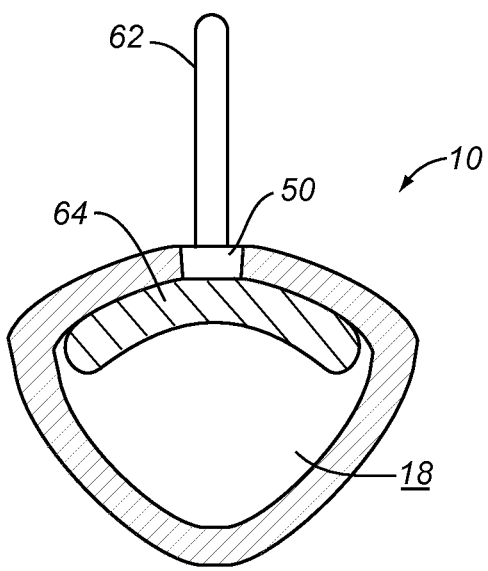

Turning to FIGS. 7A and 7B, an exemplary embodiment of a slitter device 60 is shown that may be used to slit a catheter or tubular device, such as the tubular member 10 of FIG. 1 (or any of the other embodiments herein). Generally, the slitter 60 includes a blade 62 and a wedge or "nose" segment 64 spaced apart from the blade 62, e.g., for separating the blade 62 from a pacing lead or other instrument (not shown) disposed within the accessory lumen 18 of the tubular member, and a handle 66 for manipulating the slitter device 60. The nose 64 may align and/or facilitate tracking the slitter 60 along the tubular member 10 as it is slit. In addition, the slitter 60 may include one or more features (not shown) for gripping the lead or other instrument, e.g., one or more arcuate elements extending from the nose 64 that may snap around or otherwise slidably engage the lead.

In the embodiment shown in FIG. 7B, the nose 64 may be sized to exceed the diameter of the accessory lumen 18, e.g., including an arc shape defining a radius of curvature that is greater the radius of the accessory lumen 18. Thus, when the nose 64 of the slitter 60 is inserted into the hub 30 and/or proximal end 12 of a tubular member 10, the tubular member 10 must stretch or expand to accommodate passage of the nose 64. In an exemplary embodiment, the nose 64 may have a wedge shape, e.g., having a tapered height and/or pointed on its tip, beyond the blade 62, such that the nose 64 may concentrate splitting forces on the seam 50 as the nose 64 moves longitudinally along the tubular member 10. In particular, if the filler material of the seam 50 is more elastic or softer than the base material, the filler material may stretch to increase the effective diameter of the tubular member 10 and/or decrease the wall thickness of the material at the seam 50. Thus, the filler material may stretch upward onto the wedge and into contact with the blade 62, which may then cut through the filler material to slit the seam 50. The blade 62 may be spaced from the nose 64 such that only the stretched filler material may contact the blade 62 and/or the filler material of the seam 50 may stretch and become thinner than the adjacent sidewall, which may further facilitate slitting along the seam 50. Thus, if the slitter 60 is not properly aligned with the seam 50, the blade 62 may not contact the sidewall of the tubular member 10, thereby reducing the risk of slitting at another circumferential location other than the seam 50.

Alternatively, the slitter 60 may be used to slit a seam where no filler material is used, e.g., where longitudinal edges 48 are attached directly together to provide the seam 50, yet provide lower adherence than the base material of the tubular member 10. For example, a wedge-shaped tip of the nose 64 may concentrate forces at the seam 50, and given the lower adherence of the longitudinal edges 48, the forces may cause the seam 50 to split or otherwise preferentially open, rather than causing the tubular member 10 to be cut or split elsewhere about its circumference. Once the slitter 60 passes beyond the seam 50, the blade 62 may cut through the remaining length of the tubular member 10 similar to conventional slitters. For example, the intermediate and/or distal portions 22, 24 of the tubular member 10 beyond the seam 50 may be formed from softer materials than the proximal portion 20. Thus, when the slitter 60 passes beyond the seam 50, the wedge of the nose 62 may cause the sidewall to stretch or otherwise deform to accommodate the nose 62 passing between the lead and the wall of the tubular member 10.

In addition or alternatively, a slitter may be provided that includes a relatively dull blade, e.g., incapable of cutting the reinforcing elements of the reinforcing layer 22. Thus, in this alternative, the slitter may only be capable of cutting along the seam 50 since there are no reinforcing elements along the seam 50. In a further alternative, a slitter or splitter device may be provided that includes a wedge or other nose without a blade (not shown). In this alternative, the wedge and/or nose may concentrate forces sufficiently at the seam material to cause the seam 50 to split or otherwise open up. For example, as described above, the re-welding of the longitudinal edges 48 may be intentionally weakened, e.g., by partially coating the edges 48, by providing a coated sheet through the seam 150, as shown in FIG. 3, and the like.

Figure 8:
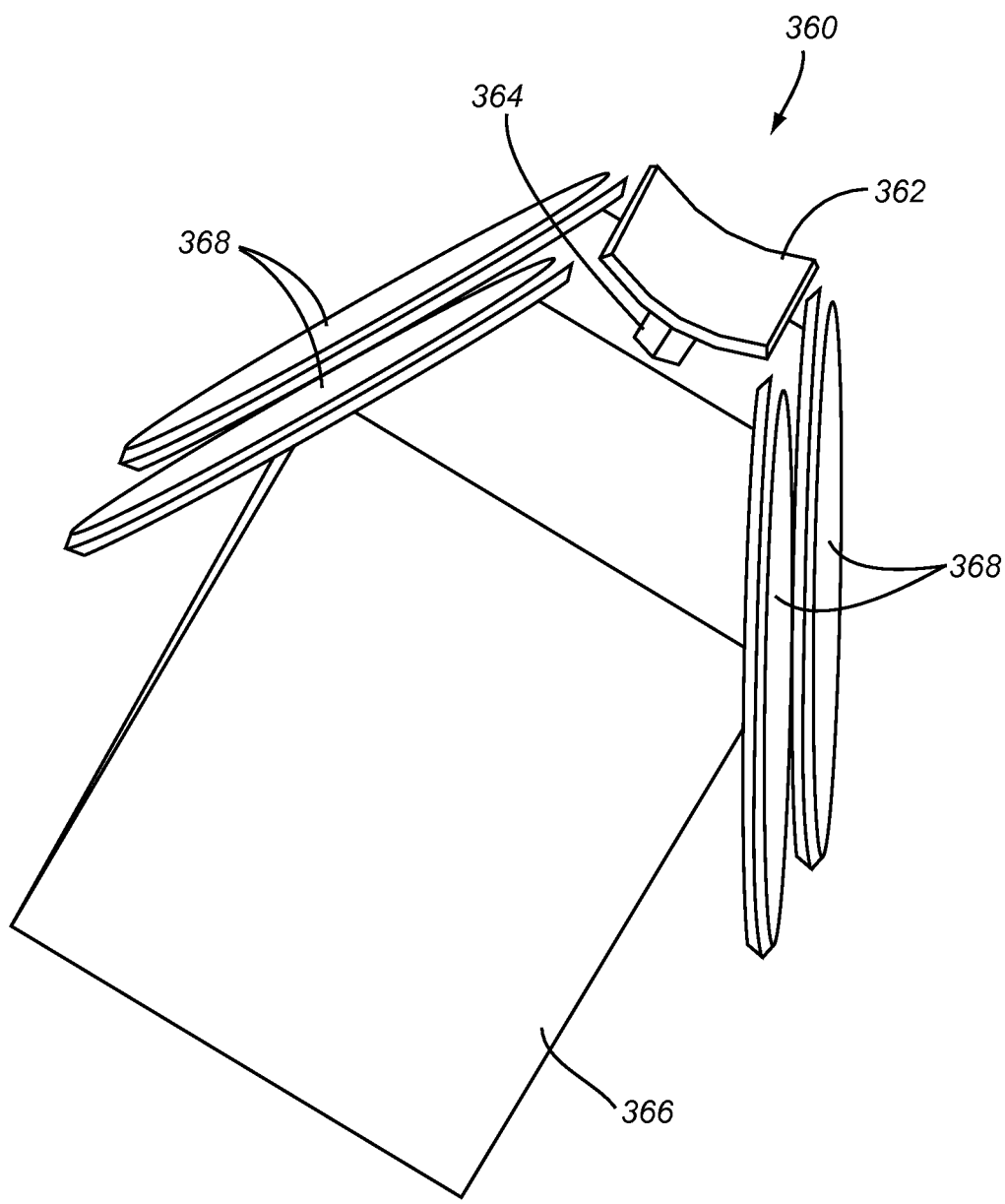
FIG. 8 is a perspective view of another exemplary embodiment of a slitter device including stabilization discs for engaging a tubular member being slit by the slitter device.

Turning to FIG. 8, another exemplary embodiment of a slitter device 360 is shown that includes a blade 364 and a one or more rotational stabilization element 368, e.g., a plurality of elements that maintain the relative rotational position of tubular member being slit (not shown) relative to the blade 364. In exemplary embodiments, the stabilization elements 368 may include one or more rotating discs, rollers, and the like (four discs shown in FIG. 8) that may grip and/or partially cut into the outer surface of the tubular member and prevent rotation.

Alternatively, FIGS. 9A-9C shows another embodiment of a slitter device 360,' which may be similar to the slitter device 360 of FIG. 8, including a plurality of rollers 368' that may engage an outer surface of a tubular member 10 being slit by the slitter device 360.' FIGS. 10A-10E show additional alternative embodiments of stabilization elements 368a-368e that may be provided on a slitter device 360a-360e. The rollers, discs, or other stabilization elements 368a-368e may substantially continuously or intermittently contact the outer surface 11 of the tubular member 10 being slit. For example, any of the stabilization elements 368 or 368a-368e may include serrations, knurling, high-tack gripping materials (not shown), and the like, which may enhance engagement with the tubular member 10. Optionally, the stabilization elements 368 may have an arcuate cross section (e.g., to increase contact area), a sharp cross section (e.g., to increase pressure without increased friction), and the like, as desired.

Figure 10F:
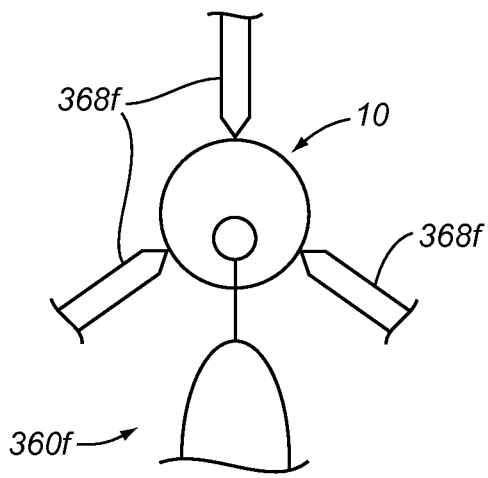
Figure 10G:
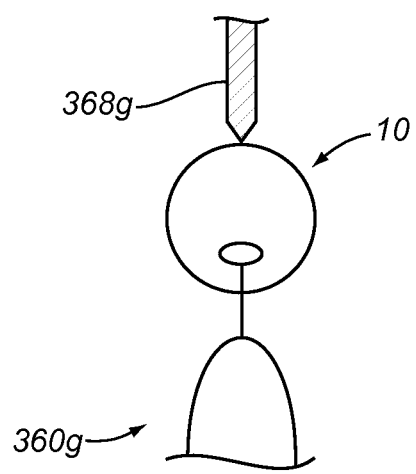
Figure 10H:
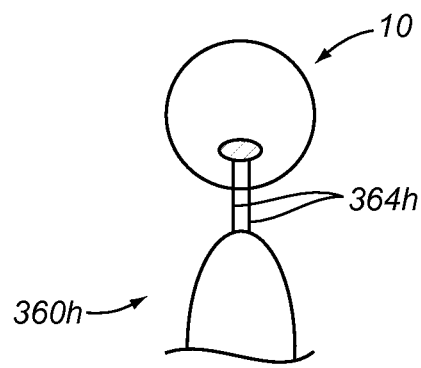

Alternatively, as shown in FIGS. 10F and 10G, a slitter device 360f, 360g may be provided in which the rollers or discs may be replaced with one or more blade-like elements 368f, 368g, which may grip and/or partially cut into the outer surface 11 of the tubular member 10 without cutting completely through the sidewall of the tubular member 10. In a further alternative, shown in FIG. 10H, a slitter device 360h may be provided that includes multiple cutting blades 364h, e.g., that simultaneously engage and slit the wall of the tubular member 10, which may also reduce the risk of spiral slitting.

Figure 11:
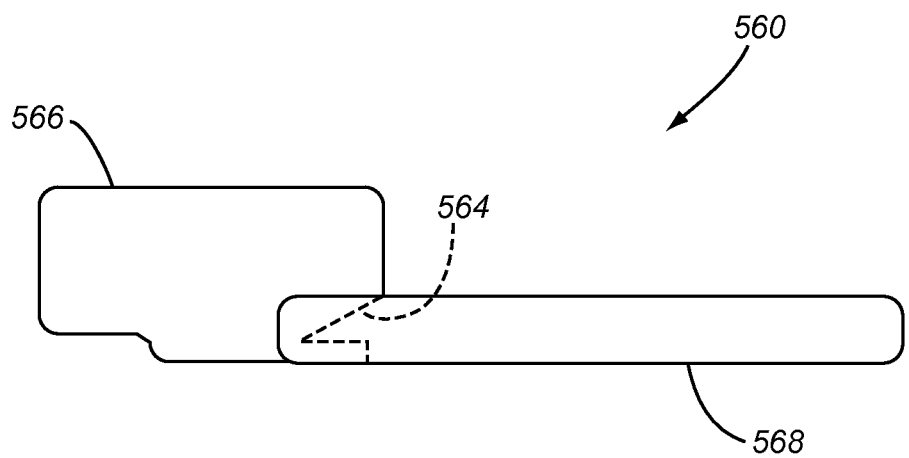
FIG. 11 is a side view of still another exemplary embodiment of a slitter device including a tubular guide member adjacent a blade of the slitter device.

Turning to FIG. 11, another embodiment of a slitter 560 is shown that includes an alignment guide 568 so that the blade 562 is maintained substantially parallel to the central longitudinal axis and/or substantially tangential to the circumference of the tubular member (not shown) being slit. Variations include long slitter nose (i.e. positioned in catheter ID) or guide tube/member (see FIG. 9) which may be C-shaped to easily place over catheter shaft. Alternatively, the guide tube/member may have two-part construction, e.g., a clam shell configuration (not shown), and the like, which may allow the guide 568 to be secured around and/or otherwise onto the tubular member, e.g. after slitting the hub of the tubular member (not shown) or otherwise accommodate for hub slitting.

Figure 12:
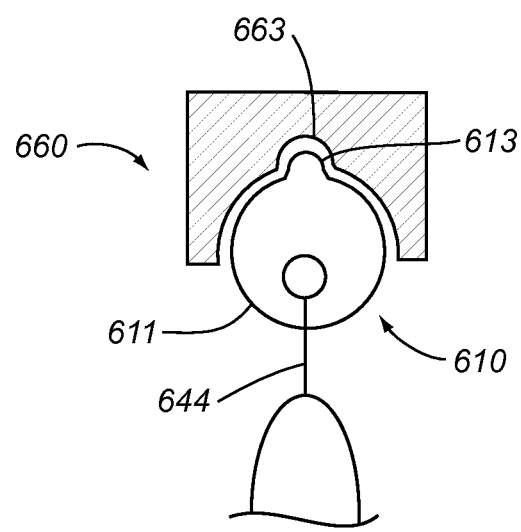
FIG. 12 is a cross-sectional view of exemplary alignment elements that may be provided on a slitter device and tubular member being slit to prevent relative rotational movement.

Turning to FIG. 12, optionally, any of the tubular members herein may include one or more alignment aid elements, e.g., a longitudinal ridge 613 provided on the outer surface 611 of the tubular member 610. The slitter device 660 may include a matching feature, e.g., a longitudinal groove 668, that may slidably receive the ridge 613 and/or otherwise enhance rotational stability of the tubular member 610 during slitting. For example, with the ridge 613 received in the groove 668, the tubular member 610 and slitter device 660 may remain rotationally aligned with one another, thereby reducing the risk of spiral slitting.

Optionally, the slitter device 660 (or any of the other slitter devices herein) may be power-driven, e.g., using one or more rollers (not shown), coupled to a motor, which allow greater motion control, e.g., substantially continuous slitting without any abrupt stops and/or starts. In addition or alternatively, any of the slitter devices herein may have the blade mounted on swivel or ball joint or other mechanism (not shown) that allows the blade to track independently, e.g., substantially straight, even if the blade becomes out of alignment position with the handle of the slitter device.

In another alternative, a roller or wheel cutter (not shown) may be provided on any of the slitter devices described herein instead of a rigid planar blade. In yet another alternative, a scissor mechanism may be provided instead of the blade shown.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A tubular device, comprising a proximal end, a distal end sized for introduction into a body lumen, and a lumen extending between the proximal and distal ends, thereby defining a longitudinal axis, the tubular device comprising:
    an inner liner surrounding the lumen and defining an inner surface;
    a reinforcing layer surrounding the inner liner, the reinforcing layer and inner liner comprising a circumferentially discontinuous portion extending from the proximal end towards the distal end at a predetermined circumferential location around the circumference of the reinforcing layer;

an outer layer surrounding the reinforcing layer and comprising base material and opposing longitudinal edges extending substantially parallel to the longitudinal axis adjacent the predetermined circumferential location, the longitudinal edges re-welded together to provide a substantially continuous outer surface for the tubular device, thereby defining a longitudinal seam in the tubular device that extends entirely between the outer and inner surfaces; and filler material disposed between the longitudinal edges and extending between the outer surface through the circumferentially discontinuous portion of the reinforcing layer and the inner liner to the inner surface, thereby defining the longitudinal seam, the filler material having a relatively low Durometer relative to the base material adjacent the longitudinal seam.

2. The tubular device of claim 1, wherein the longitudinal seam extends from the proximal end only partially towards the distal end.

3. The tubular device of claim 2, wherein the longitudinal seam has a length between about twenty five and fifty five centimeters.

4. The tubular device of claim 1, wherein the longitudinal seam extends from the proximal end along a proximal portion and terminates at an intermediate portion of the tubular device, at least one of the liner and the outer layer of the intermediate portion having one or more different mechanical properties than those of the proximal portion.

5. The tubular device of claim 4, wherein the different mechanical properties comprise at least one of stiffness, Durometer, and elasticity.

6. The tubular device of claim 1, wherein the longitudinal seam extends from the proximal end along an entire length of the tubular device to the distal end.

7. The tubular device of claim 1, further comprising a hub on the proximal end, the hub comprising one or more features at a predetermined circumferential location on the hub aligned with the longitudinal seam.

8. The tubular device of claim 1, wherein the filler material has a higher elasticity than the base material.

9. The tubular device of claim 1, wherein the reinforcing layer comprises one or more elongate elements braided substantially continuously around the circumference other than at the predetermined circumferential location.

10. The tubular device of claim 1, wherein the longitudinal edges are bonded together by reflowing at least one of the base material of the outer layer and the material of the inner liner.

11. The tubular device of claim 1, further comprising a coating at least partially applied to the longitudinal edges to reduce adhesion of the longitudinal edges to one another.

12. The tubular device of claim 1, wherein the filler material has a thickness such that the tubular device has a substantially uniform inner surface.

13. The tubular device of claim 1, further comprising a slitter device for slitting, splitting, or opening the longitudinal seam.

* * * * *